United States Patent [19]

Baccichetti et al.

[11] Patent Number: 5,179,217
[45] Date of Patent: Jan. 12, 1993

[54] METHOD OF PREPARING PHOTOCHEMOTHERAPIC ALKYLANGELICIN COMPOUNDS

[76] Inventors: Francarosa Baccichetti; Franco Bordin, both of Dipartimento di Scienze Farmaceutiche - via Marzolo, 5, 35131 Padova; Carlo Monti-Bragadin, Istitvto di Microbiologia Dell'Universita, 34127 Trieste; Francesco Carlassare, Dipartimento di Scienze Farmaceutiche - via Marzolo, 5, 35131 Padova; Giovanni Recchia, Via Aosta 16, 38100 Trento; Giovanni Rodighiero, V. A. Fusinato 50, 35100 Padova; Paolo Rodighiero, Dipart. Scienze Farmac. V. Marzolo 5, 35131 Padova; Daniela Vedaldi, Dipart Scienze Farmacevtiche V. Marzolo 5, 35131 Padova; Mario Cristofolini, V. Mariana 8, 38100 Trento; Francesco Dall'Acqua, Dipart. Scienze Farmac. V. Marzolo 5, 35131 Padova; Adriano Guiotto, Dipart. Scienze Farmac. V. Marzolo 5, 35131 Padova; Giovanni Pastorini, Dipart. Scieze Farmac V. Marzolo 5, 35131 Padova, all of Italy

[21] Appl. No.: 634,583

[22] Filed: Dec. 27, 1990

Related U.S. Application Data

[63] Continuation-in-part of Ser. No. 194,180, May 16, 1988, Pat. No. 5,001,147, which is a continuation of Ser. No. 922,342, Oct. 23, 1986, abandoned, which is a continuation of Ser. No. 541,064, Oct. 12, 1983, abandoned.

[30] Foreign Application Priority Data

Oct. 18, 1982 [IT] Italy .............................. 84148 A/82

[51] Int. Cl.$^5$ .......................................... C07D 403/00
[52] U.S. Cl. ...................................................... 549/282
[58] Field of Search ........................................ 549/282

[56] References Cited

U.S. PATENT DOCUMENTS 3,201,421  8/1965  Kaufman .............................. 549/282
4,312,883  1/1982  Bacicheti et al. ................... 549/282

Primary Examiner—C. Warren Ivy
Assistant Examiner—Raymond Covington
Attorney, Agent, or Firm—Kimmel, Crowell & Weaver

[57] ABSTRACT

The alkylangelicins according to the invention are obtained starting from an umbelliferone, in which the 6-position is already substituted by an alkyl group; in such a way the 7-allyloxy or 7-acyloxy umbelliferone intermediates can form by transposition of the allyl or acyl group only the 8-allyl and 8-acyl derivatives, and therefore the presence, even in traces, of psoralens is absolutely excluded in the subsequent synthetic steps.

The 6-alkylangelicins thus obtained are particularly usable for the photochemotherapy of psoriasys and of other skin diseases characterized by cellular hyperproliferation, as well as for the photochemotherapy of vitiligo and of alopecia aerata.

1 Claim, 8 Drawing Sheets

FIG. 1.

| COMPOUND | DARK COMPLEX WITH DNA | | DNA PHOTOBINDING | ID$_{50}$* | INHIBITION OF EPIDERMAL DNA SYNTHESIS | | | | CAPACITY TO CLEAR PSORIASIS | PIGMENTO-GENIC ACTIVITY | ERYTHEMOGENIC ACTIVITY | |
|---|---|---|---|---|---|---|---|---|---|---|---|---|
| | | | | | BY ORAL ADMINISTRATION | | BY TOPICAL APPLICATION | | | | GUINEA PIG SKIN | HUMAN SKIN |
| | K | 1/n | K x 10$^2$ min | | % | REL TO 8-MOP | % | REL TO 8-MOP | | | | |
| S-MA | 1560 | 0.071 | 3.4 | 9.1 | 38.5 | 0.98 | 47.5 | 0.78 | <8-MOP | + | − | |
| 4,5'-DMA | 1450 | 0.094 | 4.0 | 10.9 | 51 | 1.3 | 37.6 | 0.62 | <8-MOP | − | − | |
| 4',4-DMA | 6600 | 0.080 | 7.3 | 2.4 | 25.8 | 0.66 | 44.27 | 0.72 | 95% | +++ | +++ | ++/+++ |
| 4',5-DMA | 5400 | 0.080 | 5.9 | 2.6 | 53.33 | 1.36 | 58.41 | 0.95 | 100% | +++ | ++ | ++ |
| 8-MOP | 736 | 0.128 | 3.1 | 13.8 | 39.1 | 1 | 61.00 | 1 | 85% | + | ++ | + |
| 6,4'-DMA | 6300 | 0.061 | 9.9 | 2.2 | 49.2 | 1.26 | 36 | 0.52 | 95% | ++ | − | − |
| 6,4-DMA | 2990 | 0.063 | 5.23 | 4.0 | 58 | 1.48 | 47 | 0.68 | 95% | ++ | − | − |
| 4,5',6-TMA | 3310 | 0.045 | 7.2 | 3.9 | 36.8 | 0.94 | 39.6 | 0.57 | 88% | ++ | − | − |
| 6,4,4'-TMA | 10100 | 0.091 | 13.30 | 0.1 | 67 | 1.71 | 73.7 | 1.07 | 100% | ++/+++ | − | − |
| 5,5'-DMA | 1750 | 0.085 | 2.7 | 13.8 | 66.7 | 1.70 | 48.3 | 0.79 | NOT TESTED | NOT TESTED | − | NOT TESTED |
| 4,5-DMA | 6200 | 0.029 | 3.5 | 16.6 | 55 | 1.40 | 36 | 0.59 | 8-MOP | − | − | − |
| 4,5,5'-TMA | 1200 | 0.075 | 0.8 | >100 | | | NOT TESTED | | NOT TESTED | | − | NOT TESTED |

*ID$_{50}$ = DOSE OF LIGHT (365 nm) (IN TERM OF QUANTA x IC$^{18}$) NECESSARY TO PRODUCE 50% DNA SYNTHESIS INHIBITION IN EHRICH ASCITES TUMOR CELLS.

$C_{11}H_{10}O_3$ (III)

$C_{13}H_{12}O_3$ (IV)

$C_{14}H_{14}O_3$ (V)

$C_{14}H_{14}O_3$ (VI)

$C_{13}H_{12}O_3$ (VII)

FIG. 2b.

$C_{14}H_{14}O_3$
(VIII)

$C_{14}H_{14}O_3$
(IX)

$C_{15}H_{14}O_4$
(X)

$C_{16}H_{16}O_4$
(XI)

$C_{16}H_{16}O_4$
(XII)

FIG. 2c.

C$_{15}$H$_{14}$O$_4$Br$_2$
(XIII)

C$_{16}$H$_{16}$O$_4$Br$_2$
(XIV)

C$_{16}$H$_{16}$O$_4$Br$_2$
(XV)

C$_{13}$H$_{10}$O$_3$
(XVI)

C$_{14}$H$_{12}$O$_3$
(XVII)

(XVIII)

$C_{12}H_8O_3$

(XIX)

$C_{13}H_{10}O_3$

(XX)

$C_{13}H_{10}O_3$

(XXI)

$C_{12}H_{10}O_4$

(XXII)

$C_{13}H_{12}O_4$ (XXIII)

FIG. 2e.

C₁₃H₁₂O₄ (XXIV)

C₁₂H₁₀O₄ (XXV)

C₁₃H₁₂O₄ (XXVI)

C₁₃H₁₂O₄ (XXVII)

C₁₆H₁₆O₆ (XXVIII)

C₁₇H₁₈O₆ (XXIX)

FIG. 2f.

$C_{17}H_{18}O_6$ (XXX)

$C_{14}H_{12}O_6$ (XXXI)

$C_{15}H_{14}O_6$ (XXXII)

$C_{15}H_{14}O_6$ (XXXIII)

$C_{13}H_{10}O_3$ (XXXIV)

FIG. 2g.

$C_{14}H_{13}O_3$ (XXXV)

$C_{14}H_{12}O_3$ (XXXVI)

METHOD OF PREPARING PHOTOCHEMOTHERAPIC ALKYLANGELICIN COMPOUNDS

This is a continuation-in-part of Ser. No. 194,180, filed May 16, 1988 now U.S. Pat. No. 5,100,147 pending, which is a continuation of Ser. No. 922,342, filed Oct. 23, 1986, now abandoned, which is a continuation of Ser. No. 541,064, filed Oct. 12, 1983, now abandoned.

The present invention concerns a process of producing alkylangelicins (angular furocoumarins) free from psoralens (linear furocoumarin) and alkylangelicins obtained therefrom, particularly to be used for the photochemotherapy of psoriasis and of other skin diseases characterized by cellular hyperproliferation, as well as for the photochemotherapy of vitiligo and of alopecia aerata.

It is well known that the photochemotherapy of psoriasis, of mycosis fungoides and of other skin diseases characterized by cellular hyperproliferation is carried out with the combined action of psoralens (bifunctional linear furocoumarins) and long wave ultraviolet light; this therapy is also known as PUVA from psoralens-+UV-A light (320–400 nm) (Parrish et al. New Eng. J. Med.—291, 1207 (1974)).

This treatment utilizes the property of the psoralens to photodamage the skin cellular DNA in a selective way.

The antiproliferative activity is due to the mono- and bifunctional photodamages to DNA (in this latter case to inter-strand cross-links formed between two bases appertaining to the two complementary strands of the macromolecule) induced by the psoralens at cellular level.

Another property exploited by the psoralens consists in their capability of inducing the skin pigmentation; also in this case the effect is obtained through the combined action of psoralens and long wave-length ultraviolet light (UV-A). This property is used in therapy for the treatment of vitiligo or leucodermia (A.M. El Mofty "Vitiligo and psoralens" Pergamon Press, Oxford, 1968).

The PUVA therapy may be carried out either by oral administration, or by topical application of psoralens and subsequent irradiation with UV-A light.

This therapy is considered as the most effective in the case of some kinds of psoriasis, in the initial phase of mycosis fungoides and for vitiligo; however, several side effects have been evidenced, as the risk of cutaneous cancer (R. S. Stern et al "Risk of Cutaneous Carcinoma in Patients treated with oral Methoxalen Photochemotherapy for Psoriasis", N. Eng. J. Med. 300,852 (1979)), the risk of hepatoxicity (H. Tronnier et al, "Photochemotherapy in Dermatology, in "Photochemotherapy: Basic Technique and Side Effects", Proceedings of the German-Swedish Symposium on Photomedicine in Oberursel—West Germany—p. 71 Apr. 23-25, 1975, ed. E. G. Jung, Schattauer Verlag, Struttgart—New York, 1976) and of cataract (S. Lerman et al, "A Method for Detecting 8-methoxypsoralen in the Ocular Lens" Science 197,1287 (1977)) in the case of oral administration of psoralens. Furthermore the problem of the skin phototoxicity exists and it results enlarged in particular for topical application of psoralens. In fact it is well known that psoralens, also in very low doses (1-5 $\mu g/cm^2$) photoinduce a painful and troublesome erythema on the skin of the human or the guinea-pig; after some days, a dark pigmentation follows this erythema (M. A. Pathak et al. Bioassay of Natural and Synthetic Furocoumarin (psoralens), J. Inv. Dermatol, 32,509 (1959)).

Some studies concerning this object seem to indicate that the skin phototoxicity is essentially due to bifunctional lesions photoinduced in the skin cell DNA by the psoralens (F. Dall'Acqua and F. Bordin "Recent aspects of photobiological properties of furocoumarins, in the molecular basis of dermatological diseases" M. A. Pathak and P Chandra Eds. Plenum, NY in press); furthermore other studies seem to indicate that also the genotoxic effect (in terms of mutagenic activity), to which the cancerogenic activity of psoralens is clearly related, is mostly due to the cross-links (L. Dubertret et al. "Psoralens in cosmetic and dermatology" J. Cahn et al. Eds. Pergamon Press, 1981, p. 245).

In order to eliminate these undesired effects of psoralens, some monofunctional furocoumarins have been proposed, i.e. furocoumarins able to induce only monofunctional photodamages to cellular DNA. In particular it has been proposed to use the angelicin modified by introduction of one or more alkyl groups, with the aim to increase both the capacity of photoreacting with the DNA and the antiproliferative activity. In particular the alkyl groups have been introduced in 4-, 5-, 4'- and 5'-position.

The alkylangelicins thus obtained have shown a strong affinity towards DNA also in the dark; they form a molecular complex with the macromolecule and for subsequent irradiation induce very efficiently and selectively monofunctional photodamages to DNA, showing a strong antiproliferative activity.

These known alkylangelicins, and in particular the methylangelicins have shown a strong activity in the therapy of psoriasis, by topical application, showing at the same time, at the therapeutic doses, to be practically unable to cause skin phototoxicity; furthermore, their genotoxicity have proved to be generally lower than that of psoralens (U.S. Pat. No. 4,312,883).

However, the preparation of these compounds by chemical synthesis has shown some difficulties for reaching purity levels acceptable not only for laboratory search experiments on their antiproliferative activity, but most of all for their clinical experimentation. Actually the synthesis of these alkylangelicins starts from suitable O-prenyl-umbelliferones or O-acyl-umbelliferones, in which the alkyl or acyl group is rearranged (Claisen or Fries) in the 8-position. Such a transposition is not univocal, as other than in the 8-position, it occurs in the 6-position too. The 6-prenyl or 6-acyl intermediates originate, during the subsequent synthetic steps, alkylpsoralens (i.e. linear furocoumarins), which are isomers of alkylangelicins.

Considering that methylpsoralens are very effective in inducing inter-strand cross-linkages in DNA, their presence, even if in traces in the angelicins can deeply modify the photobiological and phototherapeutic properties of the same angelicins. In particular the methylpsoralens show an extremely high skin-phototoxic activity (Rodighiero et al. Il Farmaco "Photochemical and photobiological properties of 4,5'-dimethylpsoralens" Ed-Sci 36,648,1981; G. Caporale et al. "Skin Photosensitizing activity of some methylpsoralens" Experientia 23 985 (167)).

For this reason the synthesis of the above mentioned alkylangelicins involves a time-consuming an expensive step necessarily careful, concerning the separation of the essential 8-allyl intermediates or 8-acylumbelliferones from the corresponding 6-isomers.

THE SUMMARY OF THE INVENTION

According to the invention the problem is solved with a process of producing alkylangelicins free from psoralens, of formula (1)

wherein R is alkyl, $R_1$, $R_2$, $R_3$, $R_5$ are independently hydrogen or alkyl, $R_6$ is hydrogen, alkyl, hydroxymethyl, acetoxymethyl, methoxymethyl, as well as aminomethyl, alkylaminomethyl, dialkylaminomethyl or a group of formula wherein $R_7$ and $R_8$ are simultaneously hydrogen, methyl or ethyl, free or salified, characterized in that a 6-alkylumbelliferone O-derivative of formula (2)

wherein $R, R_1, R_3$ have the meaning above referred to, and $R_4$ is an acyl residue of formula wherein $R_9$ is an alkyl or an allyl residue of formula wherein $R_{10}$ and $R_{11}$ are independently hydrogen or alkyl,
or a β-ketoalkyl residue of formula wherein $R_{12}$ and $R_{13}$ are independently hydrogen or alkyl, is submitted to direct alkaline cyclization or to appropriate Fries or Claisen rearrangements and successive cyclization according to classical methods, thus yielding compound (1), wherein $R_5$ and $R_6$ are independently hydrogen or alkyl groups, and, when $R_6$ of compound (1) is hydrogen, it is converted, through a treatment with chloromethylmethylether into the corresponding 4'-chloromethylangelicin, which is then converted into the corresponding 4'-hydroxymethyl, 4'-acetoxymethyl, 4'-aminomethyl, 4'-alkylaminomethyl, 4'-dialkylaminomethyl or 4'-aminoethoxymethyl or dimethylaminoethoxymethyl or 4'-diethylaminoethoxymethyl or 4'-diethylaminoethoxymethyl derivatives and finally, to obtain water-soluble compounds, the derivatives containing the amino group, substituted or not, are converted into the corresponding hydrochlorides.

The alkylangelicins obtained through the process according to the invention are characterized by a general formula (1)

wherein R is alkyl, $R_1$, $R_2$, $R_3$ and $R_5$ are independently hydrogen or alkyl, $R_6$ is hydrogen, alkyl, hydroxymethyl, acetoxymethyl, methoxymethyl, as well as aminomethyl, alkylaminomethyl, dialkylaminomethyl or a group of formula wherein $R_7$ and $R_8$, are simultaneously hydrogen, methyl or ethyl, free or salified.

Advantageously the alkylangelicins according to the invention can be selected from the group comprising 6-methylangelicin, 6,5-dimethylangelicin, 6,5'-dimethylangelicin, 6,5,5'-trimethylangelicin, 6,4,5'-trimethylangelicin, 6,4-dimethylangelicin, 6,4'-dimethylangelicin, 6,5,4'-trimethylangelicin and 6,4,4'-trimethylangelicin.

Substantially the 6-alkylangelicins according to the present invention are obtained starting from an umbelliferone, in which the 6-position is already substituted by an alkyl group; in such a way the 7-allyloxy or 7-acyloxy umbelliferone intermediates, can form by transposition of the allyl or acyl group only the 8-allyl and 8-acyl derivatives, and therefore the presence, even in traces, of psoralens is absolutely excluded in the subsequent synthetic steps.

Synthesis of the 6-alkylangelicins

The present invention is hereinafter further clarified with reference to the following examples. Unless differently indicated, the amounts and the percentages are related to the weight.

EXAMPLE 1

A mixture of 2,4-dihydroxytoluene (18.7 g), malic acid (18.7 g) and conc. $H_2SO_4$ (37 ml) was gently heated up till the gaseous development almost ceased. The deep-red reaction mixture was then poured under vigorous stirring into boiling water (300 ml) and the suspension was kept under stirring until the gummy mass initially formed was completely dispersed. The solid was collected by filtration, dried and crystallized from absolute EtOH, yielding 6-methyl-7-hydroxycoumarin (I) (14.5 g; m.p. 253°-4° C. with dec.).

EXAMPLE 2

In a manner similar to example 1, from 3,5-dihydroxy-2-methyltoluene (9.6 g) the 5,6-dimethyl-7-hydroxycoumarin (II), crystallized from MeOH (8.5 g; m.p. 262° C. with dec.) was obtained.

EXAMPLE 3

A solution of 2,4-dihydroxytoluene (10.0 g) in ethylacetoacetate (12 ml) was poured in small portion into conc. $H_2SO_4$ (26 ml), chilling in an ice bath. After the addition was completed the solid obtained was separated by filtration, washed several times with water up to neutrality of the washings, dried and crystallized from MeOH, yielding 4,6-dimethyl-7-hydroxycoumarin (III) (10.64 g; m.p. 273° C.).

EXAMPLE 4

A mixture of 6-methyl-7-hydroxycoumarin (I) (14.5 g), anhydrous $K_2CO_3$ (5 g), allyl bromide (15 ml) and acetone (400 ml) was refluxed for 12 h under stirring. From the refluxed mixture the solid was filtered and washed several times with acetone. The acetonic solution and the pooled washings were concentrated to dryness and the residue crystallized from MeOH, yielding 6-methyl-7-allyloxycoumarin (IV) (11.4 g; m.p. 124°-5° C.).

EXAMPLES 5-6

In a manner similar to example 4, from 5,6-dimethyl-7-hydroxycoumarin (II) (5.0 g) 5,6-dimethyl-7-allyloxycoumarin (V) was obtained, crystallized from MeOH (3.8 g; m.p. 123° C.).

From 4,6-dimethyl-7-hydroxycoumarin (III) (9.6 g) 4,6-dimethyl-7-allyloxycoumarin (VI) was obtained, crystallized from MeOH (10.0 g; m.p. 134° C.).

EXAMPLE 7

A solution of 6-methyl-7-hydroxycoumarin (IV) (11.4 g) in diethylaniline (80 ml) was refluxed for 2 h. After cooling the solution was diluted with n-hexane (500 ml) yielding a precipitate, which was collected by filtration, washed several times with n-hexane and crystallized from EtOAc, yielding 6-methyl-7-hydroxy-8-allylcoumarin (VII) (6.3 g; m.p. 161°-2° C.).

EXAMPLES 8-9

In a manner similar to example 7, from 5,6-dimethyl-7-allyloxycoumarin (V) (2.0 g) 5,6-dimethyl-7-hydroxy-8-allylcoumarin (VIII) was obtained, crystallized from EtOAc/Cyclohexane (1.2 g; m.p. 169°-70° C.).

From 4,6-dimethyl-7-allyloxycoumarin (VI) (9.5 g) 4,6-dimethyl-7-hydroxy-8-allylcoumarin (IX) was obtained, crystallized from EtOAc/Cyclohexane (6.2 g; m.p. 179°-80° C.).

(IX)

(XII)

EXAMPLE 10

To prepare those alkylangelicins with an alkyl group on the furan ring, the 8-allylcoumarins were acetylated and brominated, yielding the 8-(2',3'-dibromopropyl) derivatives, which were then cyclized with ethanolic KOH, to give the corresponding 5'-methylangelicins.

In such a manner a mixture of 6-methyl-7-hydroxy-8-allylcoumarin (VII) (6.3 g), anhydrous AcONa (1.5 g) and acetic anhydride (40 ml) was refluxed for 1 h. The reaction mixture was gently diluted with water (40 ml), refluxed for 10 min and then poured into H$_2$O (300 ml) yielding a precipitate, which was collected by filtration and washed several times with H$_2$O. The dried product was crystallized from MeOH yielding 6-methyl-7-acetoxy-8-allylcoumarin (X) (6.1 g; m.p. 110°–11° C.).

(X)

EXAMPLES 11–12

In a manner similar to example 10, from 5,6-dimethyl-7-hydroxy-8-allylcoumarin (VIII) (2.5 g) 5,6-dimethyl-7-acetoxy-8-allylcoumarin (XI) was obtained, crystallized from MeOH (2.2 g; m.p. 148°–9° C.);

(XI)

From 4,6-dimethyl-7-hydroxy-8-allylcoumarin (IX) (3 g) 4,6-dimethyl-7-acetoxy-8-allylcoumarin (XII) was obtained, crystallized from MeOH (2.4 g; m.p. 139°–140° C.).

EXAMPLE 13

Into an acetic solution (100 ml) of 6-methyl-7-acetoxy-8-allylcoumarin (X) (7 g) an acetic solution (50 ml) containing the stoichiometric amount of bromine was added dropwise at room temperature.

After the addition was completed the solution was stirred for 30 min., the solvent was evaporated under reduced pressure and the solid residue crystallized from MeOH giving the 6-methyl-7-acetoxy-8-(2',3'-dibromopropyl) coumarin (XIII) (6.8 g; m.p. 154°–5° C.).

(XIII)

EXAMPLES 14–15

In a manner similar to example 13 from 5,6-di-methyl-7-acetoxy-8-allylcoumarin (XI) (2.6g) 5,6-dimethyl-7-acetoxy-8-(2',3'-dibromopropyl)coumarin (XIV) was obtained, crystallized from MeOH (2.1 g; m.p. 168°–9° C.).

(XIV)

From 4,6-dimethyl-7-acetoxy-8-allylcoumarin (XII) (2.3 g) 4,6-dimethyl-7-acetoxy-8-(2',3'-dibromopropyl)-coumarin (XV) was obtained, crystallized from MeOH (1.5 g; m.p. 135°–137° C.).

(XV)

EXAMPLE 16

To an ethanolic solution (100 ml) of 6-methyl-7-acetoxy-8-(2',3'-dibromopropyl) coumarin (XIII) (1.5 g) a volume of ethanolic 4% KOH solution was added, equivalent to a molar ratio coumarin/KOH 1:10. The mixture was refluxed for 80 min. in the dark, chilled, diluted with H₂O (200 ml) and acidified with dil. HCl. The precipitate thus obtained was filtered, washed with H₂O, dried and chromatographed on a silica gel column by eluting with CHCl₃, yielding the 6,5'-dimethylangelicin (XVI), crystallized from MeOH (0.52 g; m.p. 175°–6° C.).

EXAMPLES 17–18

In a manner similar to example 16 from 5,6-di-methyl-7-acetoxy-8-(2',3'-dibromopropyl)coumarin (XIV) (1.07 g) 6,5,5'-trimethylangelicin (XVII) was obtained, crystallized from MeOH (0.38 g; m.p. 204°–5° C.).

From 4,6-dimethyl-7-acetoxy-8-(2',3'-dibromopropyl)coumarin (XV) (2.1 g) 6,4,5'-trimethylangelicin (XVIII) was obtained, crystallized from MeOH (0.62 g; m.p. 183° C.).

EXAMPLE 19

The following procedure is used to prepare the alkylangelicins without alkyl groups on the furan ring. The 8-allyl derivatives of the coumarins (VII), (VIII), (IX) were ozonized and then reduced, thus yielding the 8-coumarinylacetaldehydes, which were then cyclized with 85% H₃PO₄.

The 6-methyl-7-hydroxy-8-allylcoumarin (VII) (1.7 g) was dissolved in EtOAc (150 ml) and into the solution, cooled in an ice bath, a stream of ozonized oxigen was bubbled until 1.1 times the stoichiometric amount of ozone was reached. The solution was then immediately submitted to hydrogenation in the presence of Pd 10% on CaCO₃ (0.3 g) and the mixture stirred until the rapid absorption of hydrogen ceased. The catalyst was removed by filtration, the solvent evaporated at reduced pressure, and the residue treated with 85% H₃PO₄ (60 ml). The reaction mixture was then placed into a thermostatic bath at 100° C. for 20 min, chilled, diluted with H₂O (200 ml) and extracted with CHCl₃. From the dried (Na₂SO₄) organic phase the solvent was evaporated under reduced pressure and the residue chromatographed on a silica gel column by eluting with CHCl₃, yielding the 6-methylangelicin (XIX), crystallized from MeOH (0.18 g; m.p. 164°–5° C.).

EXAMPLES 20–21

In a manner similar to example 19 from 5,6-di-methyl-7-hydroxy-8-allylcoumarin (VIII) (2.0 g) the 6,5-dimethylangelicin (XX) was obtained, crystallized from MeOH (0.21 g; m.p. 219°–20° C.).

From 4,6-dimethyl-7-hydroxy-8-allylcoumarin (IX) (3.2 g) the 6,4-dimethylangelicin (XXI) was obtained, crystallized from MeOH (0.42 g; m.p. 150°–1° C.).

EXAMPLE 22

To prepare the alkylangelicins with an alkyl group in the 4'-position of the furan ring, the suitable umbelliferones, (I), (II), (III) were acetylated and the 7-acetoxycoumarins thus obtained were submitted to the Fries rearrangement. The 8-acetylumbelliferones were converted into the ethyl esters of the 7-(8-a-cetyl-coumarinyl)oxyacetic acids, which were then hydrolized and cyclized yielding the desired 4'-methylangelicins. In such a manner a mixture of 6-methyl-7-hydroxycoumarin (I) (10.0 g), acetic anhydride (40 ml) and anhydrous AcONa (4.0 g) was refluxed for 1 h. To the reaction mixture an equal volume of H₂O was cau- tiously added and the whole was refluxed for 10 min. The mixture was diluted with H₂O (300 ml), chilled and the precipitate was collected by filtration, washed several times with H₂O, dried and crystallized from MeOH, yielding the 6-methyl-7-acetoxycoumarin (XXII) (10.0 g; m.p. 147° C.).

(XXII)

EXAMPLES 23-24

In a manner similar to example 22 from 5,6-di-methyl-7-hydroxycoumarin (II) (5.0 g) 5,6-dimethyl-7-acetoxycoumarin (XXIII) was prepared, crystallized from MeOH (4.6 g; m.p. 206° C.).

(XXIII)

From 4,6-dimethyl-7-hydroxycoumarin (III) (8.0 g) 4,6-dimethyl-7-acetoxycoumarin (XXIV) was prepared, crystallized from MeOH (7.8 g; m.p. 160°-1° C.).

(XXIV)

EXAMPLE 25

A mixture of 6-methyl-7-acetoxycoumarin (XXII) (2.0 g), anhydrous AlCl₃ (4.4 g) and NaCl (2.0 g) was heated at 160°-170° C. for 1.5 h. The reaction mixture, after cooling was disgregated in dil. HCl (50 ml), refluxed for 10 min, then poured into H₂O (200 ml) and extracted with EtOAc. The dried organic phase (Na₂SO₄) gave by evaporation of the solvent a residue which was crystallized from MeOH yielding the 6-methyl-7-hydroxy-8-acetylcoumarin (XXV) (1.1 g; m.p. 170° C.).

(XXV)

EXAMPLES 26-27

In a manner similar to example 25, from 5,6-di-methyl-7-acetoxycoumarin (XXIII) (3.0 g) 5,6-dimethyl-7-hydroxy-8-a-cetylcoumarin (XXVI) was obtained, crystallized from EtOAc (0.95 g; m.p. 216°-8° C.).

(XXVI)

From 4,6-dimethyl-7-acetoxycoumarin (XXIV) (3 g) 4,6-dimethyl-7-hydroxy-8-acetylcoumarin (XXVII) was obtained, crystallized from MeOH (1.05 g; m.p. 236°-7° C.).

(XXVII)

EXAMPLE 28

A mixture of 6-methyl-7-hydroxy-8-acetylcoumarin (XXV) (1.8 g) and of ethyl bromoacetate (3 ml) dissolved into acetone (50 ml) and in the presence of anhydrous K₂CO₃ was refluxed for 3 h. After cooling the solid was eliminated by filtration and the solvent evaporated under reduced pressure. The residue was crystallized from EtOAc/cyclohexane yielding the ethyl ester of the 7-(6-methyl-8-a-cetylcoumarinyl)oxyacetic acid (XXVIII) (1.7 g; m.p. 88°-9° C.).

(XXVIII)

EXAMPLES 29-30

In a manner similar to example 28 from 5,6-di-methyl-7-hydroxy-8-acetylcoumarin (XXVI) (1.4 g) the ethyl ester of the 7-(5,6-dimethyl-8-acetylcoumarinyl)oxyacetic acid (XXIX) was obtained, crystallized from EtOAc/cyclohexane (0.8 g; m.p. 109° C.).

(XXIX)

From 4,6-dimethyl-7-hydroxy-8-acetylcoumarin (XXVII) (3.2 g) the ethyl ester of the 7-(4,6-dimethyl-8-acetylcoumarinyl)oxyacetic acid (XXX) was obtained, crystallized from EtOAc/cyclohexane (2.2 g; m.p. 96°-7° C.).

(XXX)

EXAMPLE 31

The ethyl ester of the 7-(6-methyl-8-acetyl-coumarinyl)oxyacetic acid (XXVIII) (1.8 g) was dissolved into a water-methanolic solution (1/1) of 5% KOH (70 ml) and the solution was refluxed for 15 min, in the dark. After cooling and acidification with dil. HCl, the solution was diluted with H$_2$O (200 ml) and the solid precipitate was collected by filtration, dried and crystallized from EtOAc/cyclohexane, yielding the 7-(6-methyl-8-acetylcoumarinyl)oxyacetic acid (XXXI; 1.1 g; m.p. 196°–7° C.).

(XXXI)

EXAMPLES 32–33

In a manner similar to example 31, from the ethyl ester of the 7-(5,6-dimethyl-8-acetylcoumarinyl)oxyacetic acid (XXIX) (1.7 g) the 7-(5,6-dimethyl-8-acetylcumarinyl)oxyacetic acid (XXXII) was obtained, crystallized from MeOH (1.3 g; m.p. 219°–20° C.).

(XXXII)

From the ethyl ester of the 7-(4,6-dimethyl-8-acetylcoumarinyl)oxyacetic acid (XXX; 1.9 g) the 7-(4,6-dimethyl-8-acetylcoumarinyl)oxyacetic acid (XXXIII) was obtained, crystallized from EtOAc (1.35 g; m.p. 184°–6° C.).

(XXXIII)

EXAMPLE 34

A mixture of 7-(6-methyl-8-acetylcoumarinyl)oxyacetic acid (XXXI; 3.7 g), anhydrous AcONa (3 g) and acetic anhydride (30 ml) was refluxed for 1 h. In such conditions the compound (XXXI) underwent cyclization also accompanied by a nearly complete decarboxylation. To the mixture H$_2$O (30 ml) was gently added and the whole was again refluxed for 10 min. The cooled reaction mixture was diluted with H$_2$O (300 ml), made alkaline by NaHCO$_3$ addition and the suspension was extracted several times with EtOAc. From the dried organic phase (Na$_2$SO$_4$) the solvent was evaporated and the residue crystallized from MeOH, yielding the 6,4'-dimethylangelicin (XXXIV; 2.1 g; m.p. 156°–7° C.).

(XXXIV)

EXAMPLES 35–36

In a manner similar to example 34 from the 7-(5,6-dimethyl-8-acetylcoumarinyl)oxyacetic acid (XXXII) (2.2 g) the 6,5,4'-trimethylangelicin (XXXV) was obtained, crystallized from MeOH (1.15 g; m.p. 229° C.).

(XXXV)

From the 7-(4,6-dimethyl-8-acetylcoumarinyl)oxyacetic acid (XXXIII; 1.7 g) the 6,4,4'-trimethylangelicin (XXXVI) was obtained, crystallized from MeOH (0.85 g; m.p. 201°–2° C.).

(XXXVI)

EXAMPLE 37

A mixture of 4,6-dimethyl-7-hydroxycoumarin (III) (5.0 g), anhydrous K$_2$CO$_3$ (10 g), chloroacetone (2.5 ml) and acetone (150 ml) was refluxed for 12 h under stirring. From the refluxed mixture the solid was filtered and washed several times with acetone. The acetonic solution and the pooled washings were concentrated to dryness and the residue crystallized from MeOH, yielding 4,6-dimethyl-7-acetonyloxycoumarin (XXXVII) (5.1 g; m.p. 190° C.)

EXAMPLE 38

To an ethanolic solution (500 ml) of 4,6-dimethyl-7-acetonyloxycoumarin (XXXVII) (10.0 g) a volume of ethanolic 5% KOH solution was added, equivalent to a molar ratio coumarin/KOH 1:5. The mixture was refluxed 30 min in the dark, chilled, poored into a water-ice mixture (1000 ml) and acidified with diluted HCl. The precipitate thus obtained was filtered, washed with H₂O, dried and crystallized from MeOH yielding the 4,6,4'-trimethylangelicin (XXXVI) (5.75 g; m.p. 201°–202° C.).

DISCUSSION OF THE PHARMACOLOGICAL PROPERTIES OF THE 6-ALKYLANGELICINS

The 6-alkylangelicins according to the invention show an appreciable technical progress with respect to the known alkylangelicins, and this either under the aspect of the therapeutic security, being they absolutely free from psoralens, or under the aspect of the preparation facility.

In fact the total lacking of psoralens make sure that the high antiproliferative activity is only due to monofunctional lesions to DNA, and at the same time allows to obtain a compound through a process more quick, more simple, less expensive and having a higher efficiency.

PHOTOBINDING CAPACITY OF THE 6-ALKYLANGELICINS TO DNA

Figure 1:
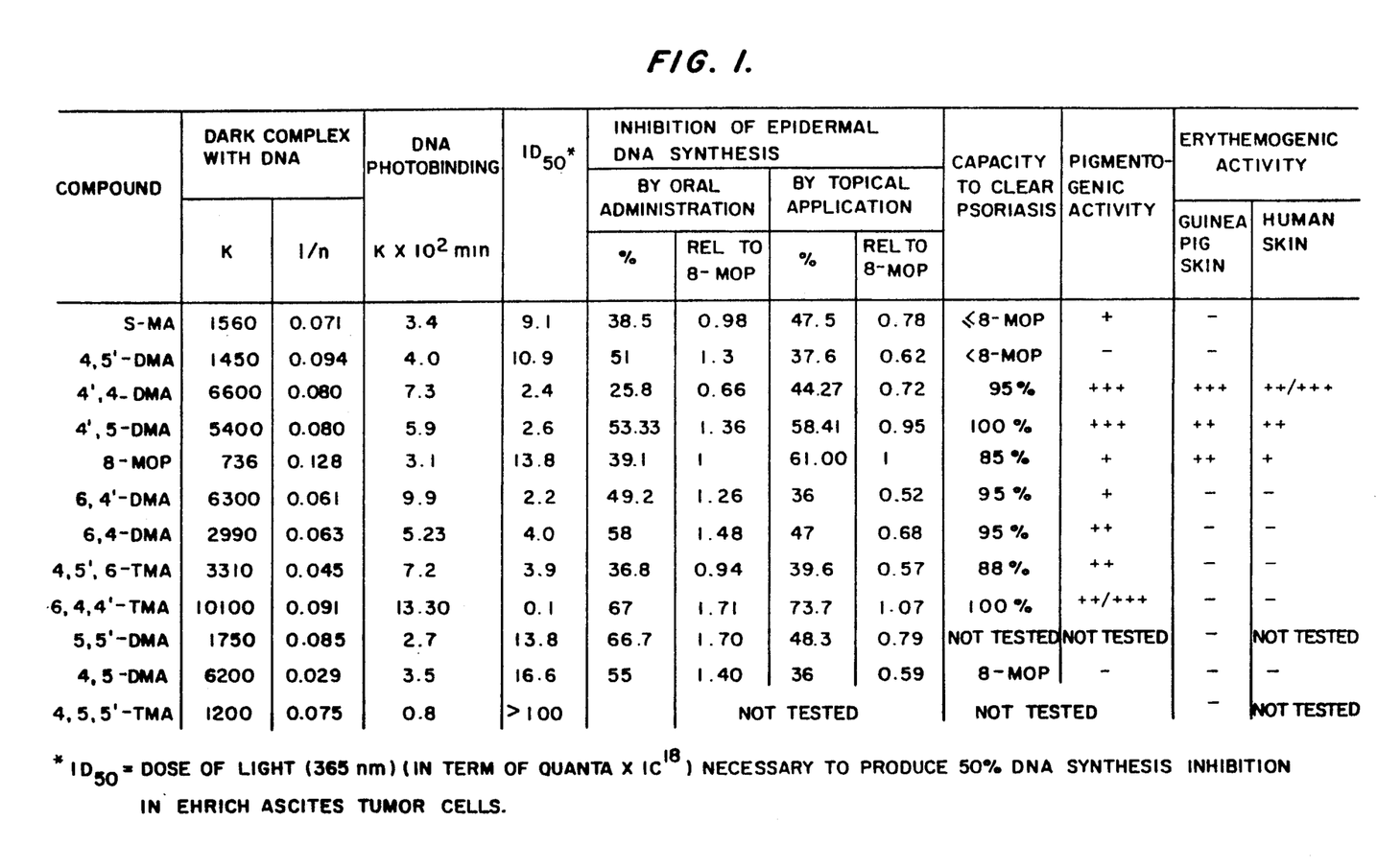
FIG. 1 is a table showing a summary of the test results obtained with various other compounds identified herein.
Figure 2A:
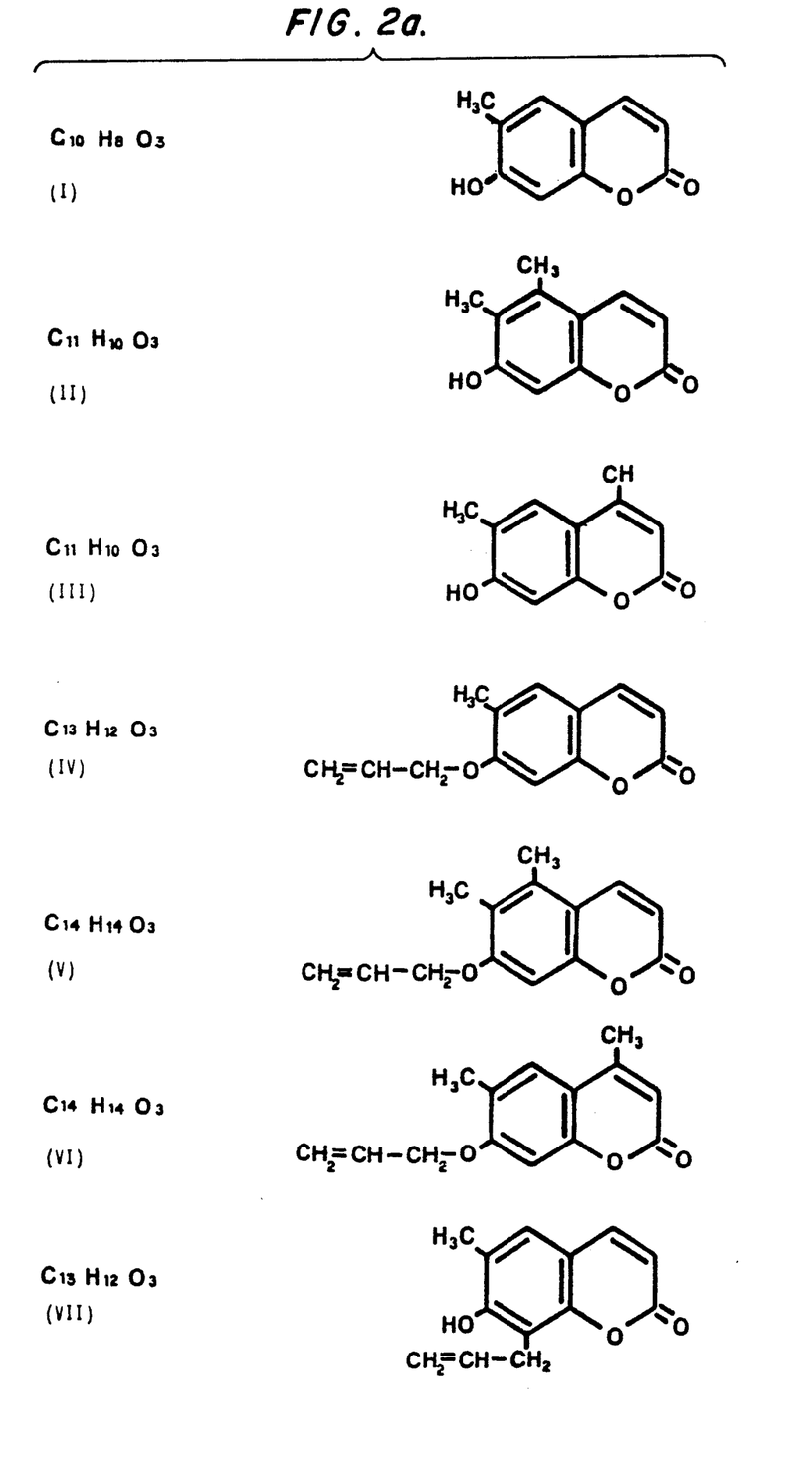
FIGS. 2A-2G are empirical and structural formulas of the compounds identified herein I-XXXVI.
Figure 2B:
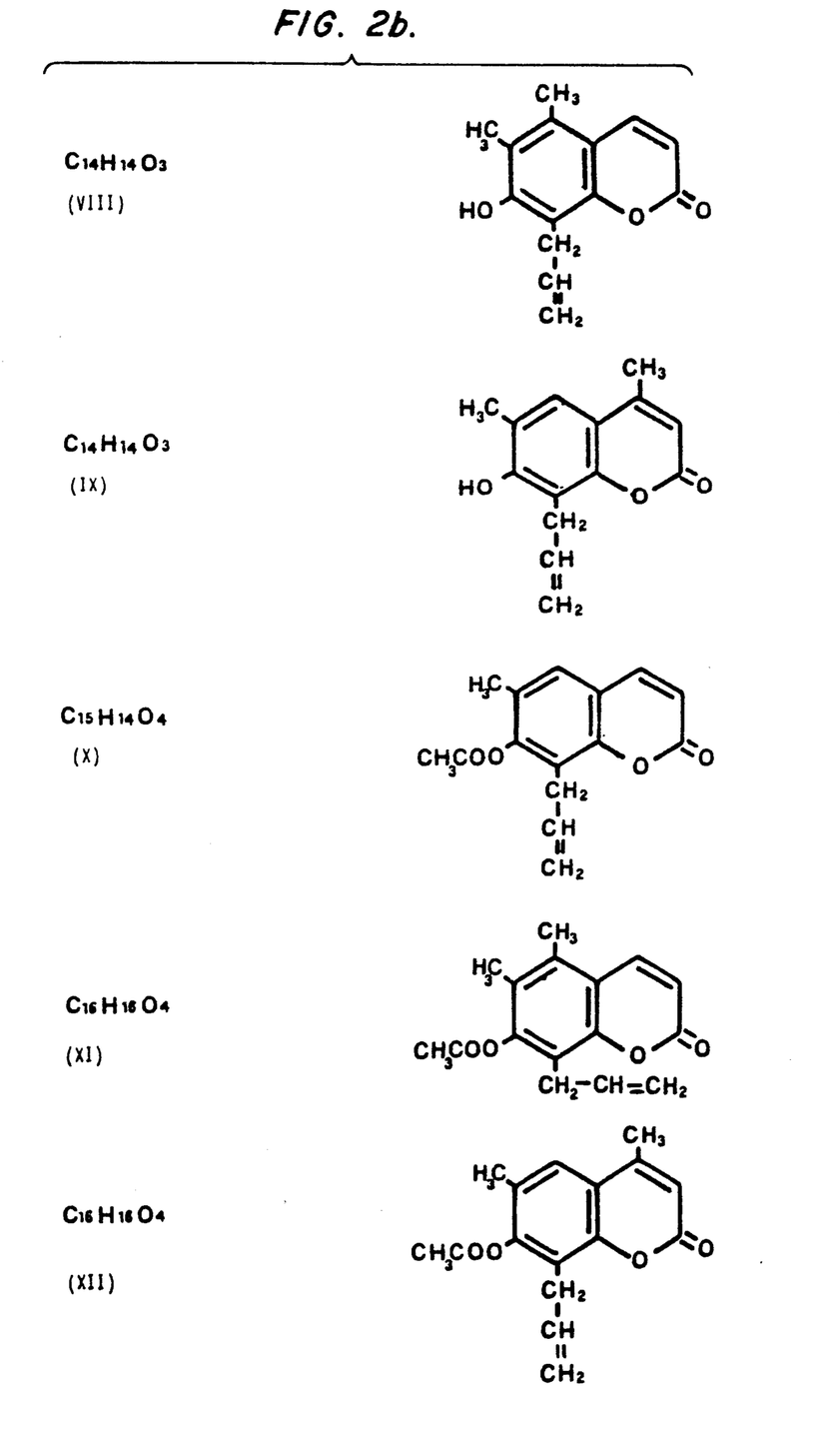
Figure 2C:
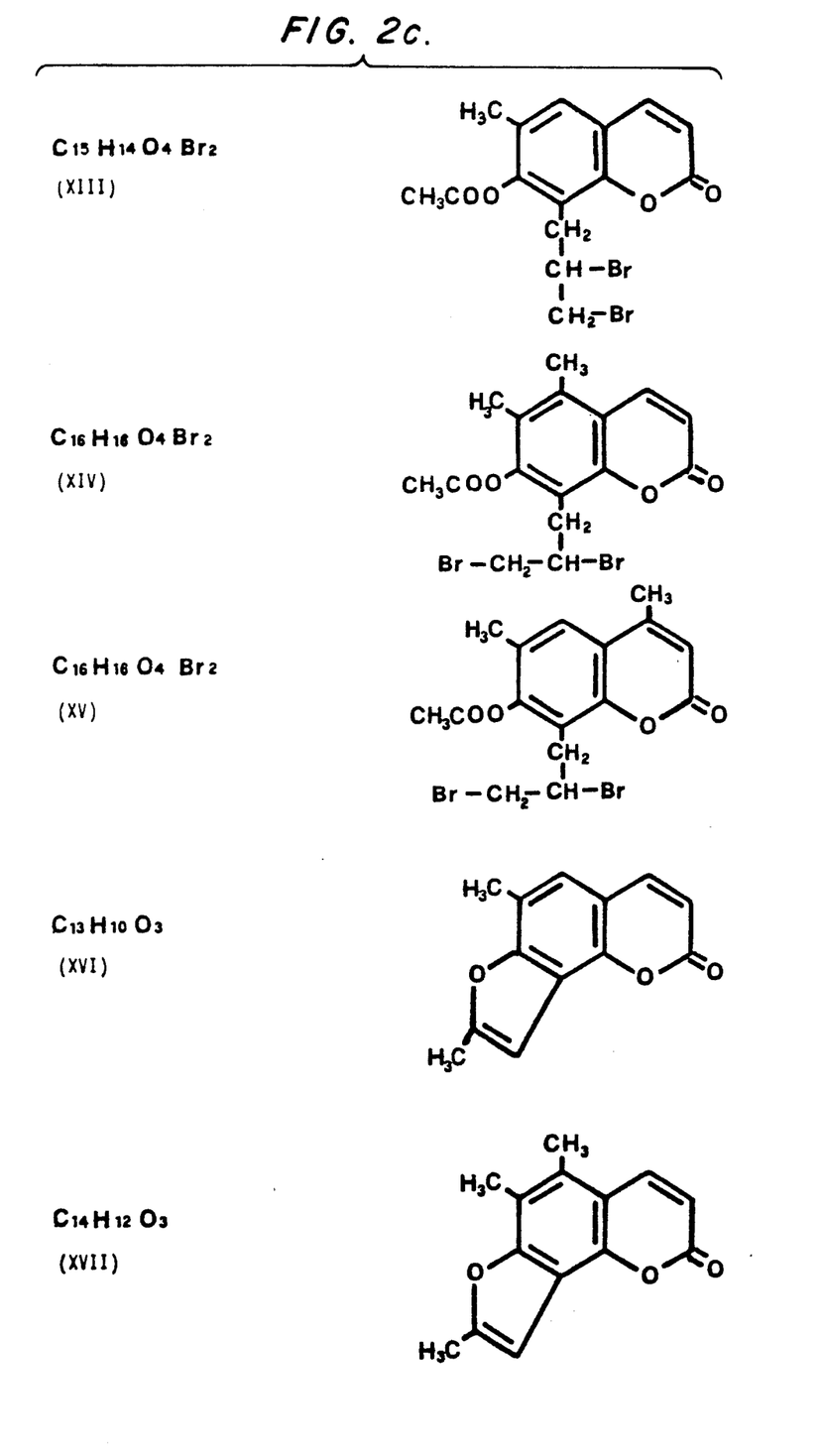
Figure 2D:
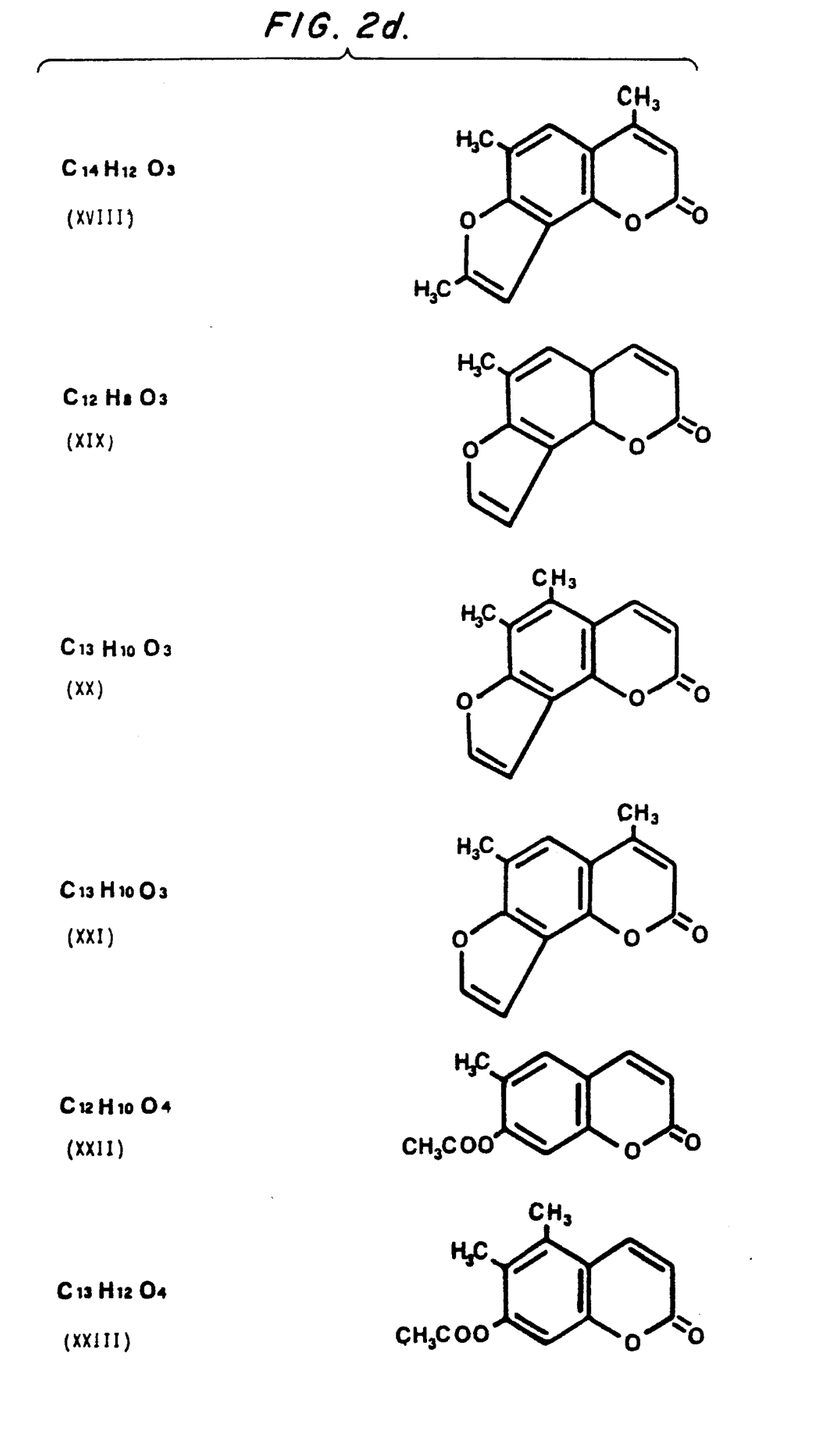
Figure 2E:
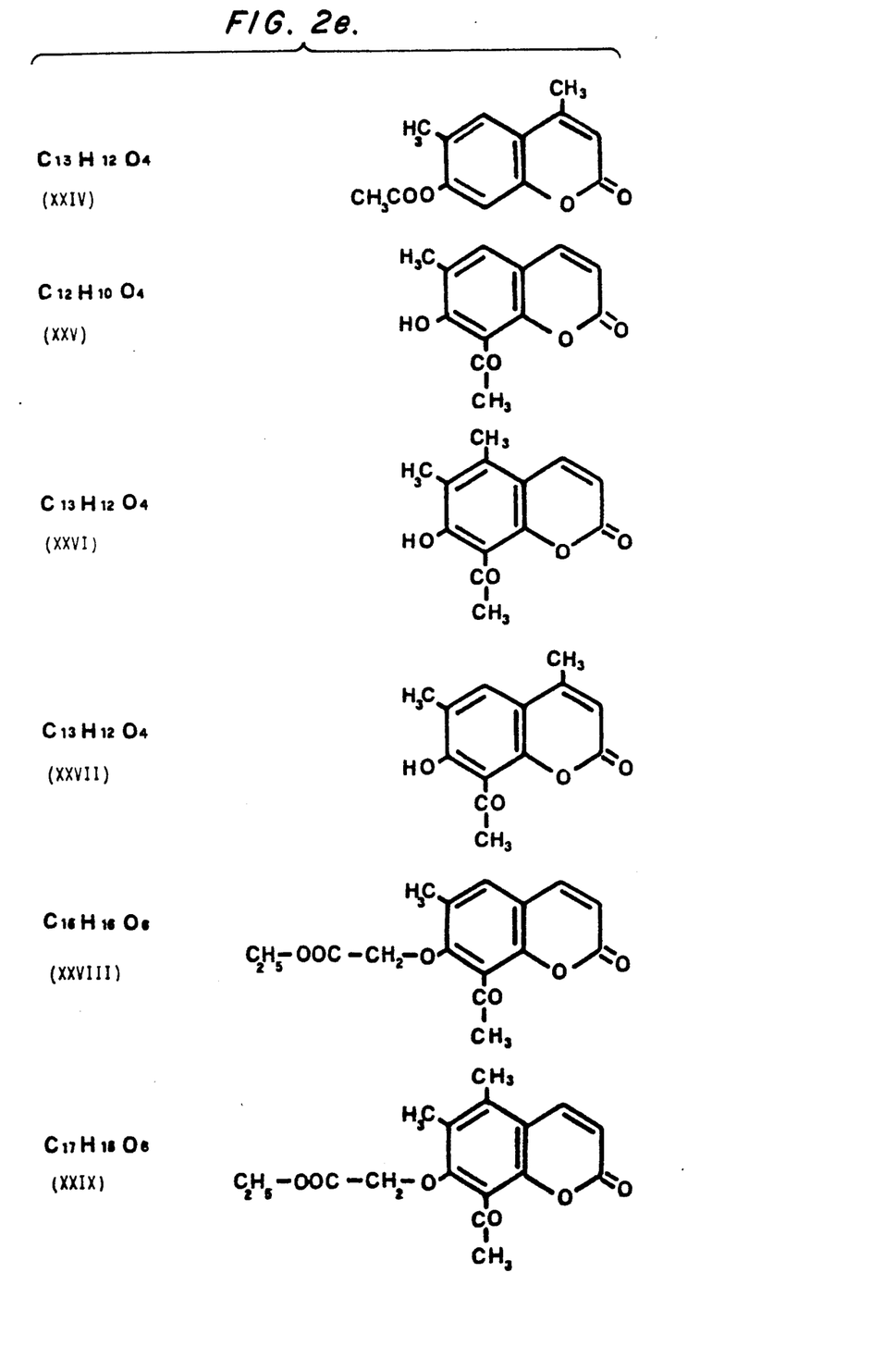
Figure 2F:
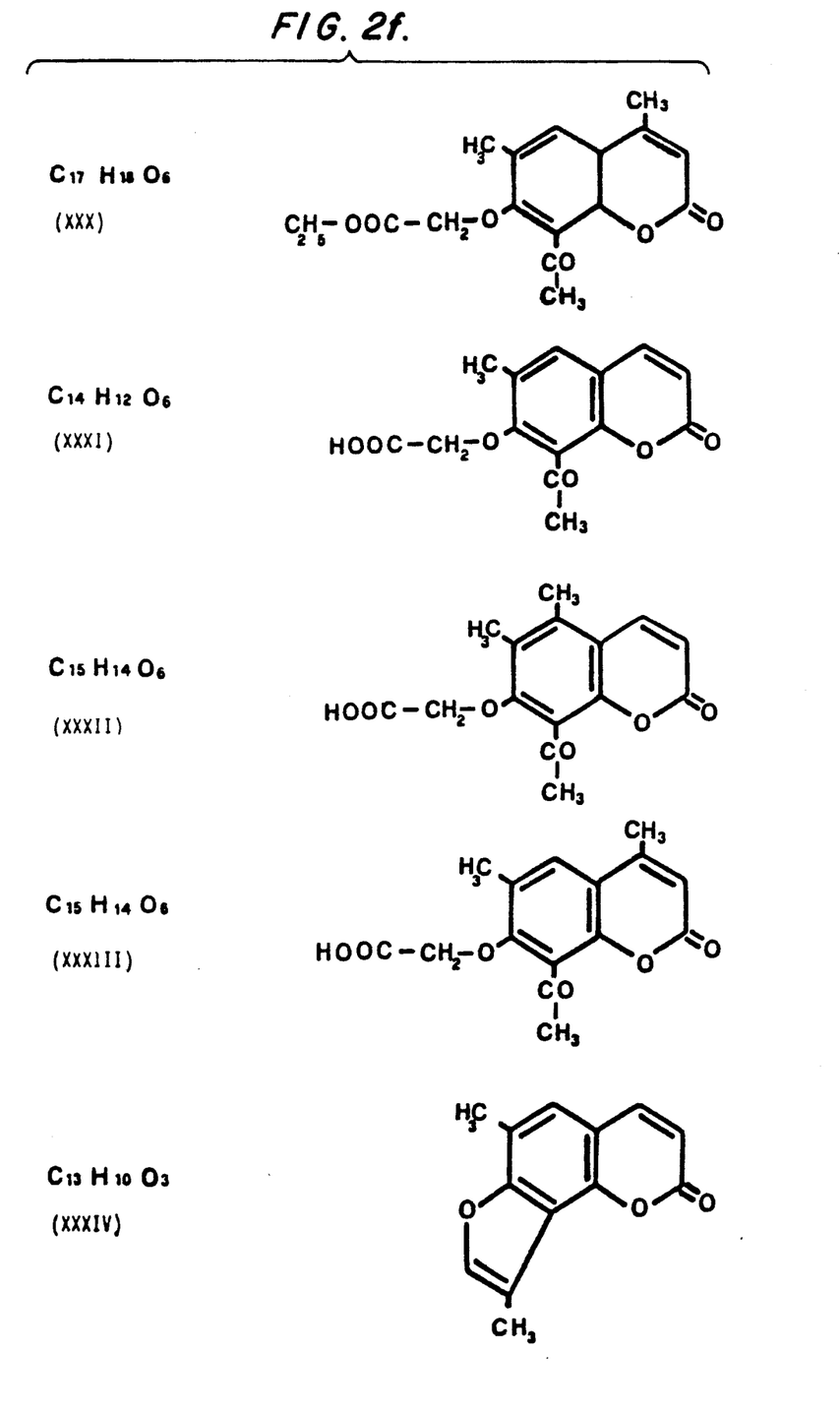
Figure 2G:
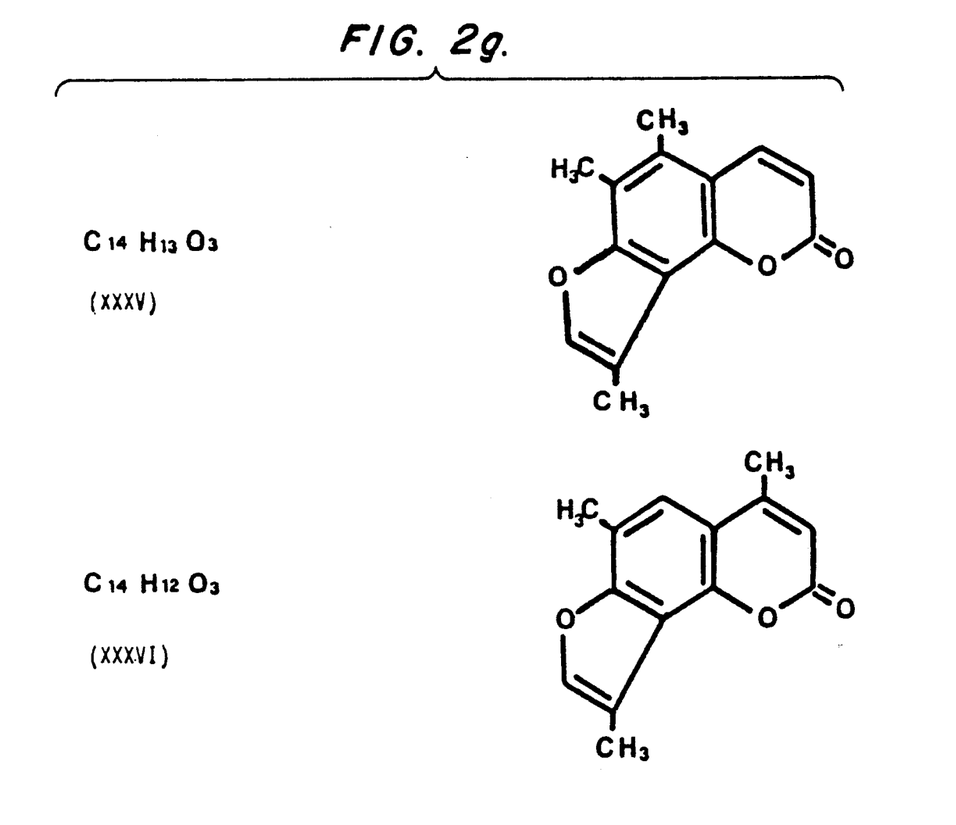

The 6-alkylangelicins show a strong affinity with DNA in the dark, thus forming molecular intercalated complexes; moreover the 6-methylangelicins complexed to DNA by irradiation bind very strongly to the macromolecule, inducing only monofunctional lesions (Table I).

ANTIPROLIFERATIVE ACTIVITY OF THE 6-ALKYLANGELICINS IN PRECLINICAL TESTS

The 6-alkylangelicins show a strong antiproliferative activity in Ehrlich ascites tumor cells (Table II) and on the skin of mice in terms of DNA synthesis inhibition (Table III). These compounds are practically unable to induce skin phototoxicity on albino guinea-pig skin (Table II).

TABLE I

Binding parameters of the complexes between 6-alkylangelicins and DNA and rate constant of their photoreactions with the macromolecule.

| Compound | K values | $\underline{n}^a$ | $1/\underline{n}^b$ | rate constant × min$^{-1}$ × 10$^2$ |
|---|---|---|---|---|
| angelicin | 560 | 15.87 | 0.063 ± 0.003 | 1.10 |
| 6-methylangelicin | 925 ± 64 | 20.83 | 0.048 ± 0.002 | 3.60 |
| 6,4-dimethylangelicin | 2,990 ± 232 | 15.87 | 0.063 ± 0.003 | 5.23 |
| 6,4'-dimethylangelicin | 6,300 ± 541 | 16.39 | 0.061 ± 0.003 | 9.90 |
| 6,5'-dimethylangelicin | 1,975 ± 136 | 12.82 | 0.078 ± 0.004 | 3.00 |
| 6,4,4'-trimethylangelicin | 10,100 ± 1190 | 10.99 | 0.091 ± 0.0045 | 13.30 |
| 6,4,5'-trimethylangelicin | 3,310 ± 281 | 22.22 | 0.045 ± 0.002 | 7.02 |
| 6,5,5'-trimethylangelicin | 3,730 ± 339 | 14.29 | 0.070 ± 0.0035 | 2.30 |
| 8-MOP$^c$ | 736$^c$ | 7.81$^c$ | 0.128$^c$ | 3.10 |

$^a$According to Mc Ghee and Von Hippel, (J.Mol. Biol., 86, 469, 1974), $\underline{n}$ is defined here as the number of nucleotides occluded by one bound molecule of angelicin derivative.
$^b$1/$\underline{n}$ defines, according to Mc Ghee and Von Hippel, the frequency of binding sites; in other words, the number of ligands bound per nucleotide, and can be considered analogous to the "$\underline{n}$" value obtained by the classic Scratchard method (Ann. N.Y. Acad. Sci., 51, 660, 1949).
$^c$As reference compound; data taken from Dall'Acqua et al. J. Invest. Dermatol., 29, 283, 1979.

TABLE II

Photobiological properties of 6-alkylangelicins

| Furocoumarin | Inhibition of DNA synthesis in Ehrlich ascites tumor cells (a) | | skin erythemogenic activity (a) |
|---|---|---|---|
| | ID$_{50}$(quanta × 10$^{-18}$) ± S.E. | Relative activity | |
| 8-MOP (b) | 13.8 ± 0.6 | 181 | ++ |
| angelicin | 25.0 ± 1.1 | 100 | — |
| 6-methylangelicin | 26.3 ± 1.4 | 95 | — |
| 6,4-dimethylangelicin | 4.0 ± 1.3 | 625 | — |
| 6,4'-dimethylangelicin | 2.28 ± 0.68 | 1096 | — |
| 6,5'-dimethylangelicin | 11.87 ± 0.77 | 210 | — |
| 6,4,5'-trimethylangelicin | 3.87 ± 1.5 | 646 | — |
| 6,4,4'-trimethylangelicin | 0.06 ± 0.007 | 41666 | — |

(a) Determined according to Bordin et al., Il Farmaco, Ed.Sc., 36, 506, 1981.
(b) As reference sample.

TABLE III

Inhibition of epidermal DNA synthesis in the mouse "in vivo" after topical application (50 μg/cm²) of the compound and UV-A irradiation (9 J/cm²) (a).

| Furocoumarin | % inhibition ± S.E. |
|---|---|
| No drug solvent alone | 2.5 ± 1.3 |
| 8-MOP (b) | 61.0 ± 1.6 |
| angelicin (b) | 17.5 ± 2.5 |
| 6-methylangelicin | 29.25 ± 13.3 |
| 6,4-dimethylangelicin | 47.05 ± 4.3 |
| 6,4'-dimethylangelicin | 36.56 ± 3.9 |
| 6,5-dimethylangelicin | 52.83 ± 2.3 |
| 6,5,5'-trimethylangelicin | 36.01 ± 11.7 |

(a) Determined according to Bordin et al., Il Farmaco, Ed.Sc., 36, 506, 1981.
(b) Reference compounds.

CAPACITY TO INDUCE DARK PIGMENTATION ON HUMAN SKIN

The 6-alkylangelicins are able to induce a dark pigmentation on human skin, without however inducing erythema at the therapeutical doses (Table IV).

TABLE IV

Results of topical photochemotherapy with 6-alkylangelicins in psoriatic patients.

| No | NAME | SEX | 6-METHYL ANGELICINS (6-MA) | MAXIMA DOSE OF UV-A | No OF TREATMENTS | % CLEARANCE | | ERYTHEMA INDUCTION | | PIGMENTAL CAPACITY | |
|----|------|-----|---------------------------|--------------------|-----------------|------------|------|-------------------|-------|-------------------|------|
| | | | | | | 6-MA | 8-MOP | 6-MA | 8-MOP | 6-MA | 8-MOP |
| 1 | P.G. | M. | 6,4'-DMA | 8 J/cm$^2$ | 15 | 100% | 85% | — | — | + | ++ |
| 2 | M.S. | F. | 6,4'-DMA | 9 J/cm$^2$ | 15 | 90% | 70% | — | + | + | ++ |
| 3 | B.M. | F. | 6,4,4'-TMA | 8 J/cm$^2$ | 11 | 100% | 75% | — | + | +++ | + |
| 4 | U.A. | F. | 6,4,4'-TMA | 4 J/cm$^2$ | 11 | 95% | | — | +++a) | + | — |
| 5 | D.B.V. | F. | 6,4,4'-TMA | 10 J/cm$^2$ | 15 | 90% | 90% | — | +++ | ++ | + |
| 6 | F.B. | F. | 6,4,4'-TMA | 6 J/cm$^2$ | 9 | 100% | 80% | — | +++b) | + | + |
| 7 | C.M.P. | F. | 6,4,4'-TMA | 6 J/cm$^2$ | 9 | 100% | 85% | — | ++ | + | ++ | a) The treatment with 8-MOP was stopped after 4 applications for severe bollous reaction.
b) The treatment with 8-MOP was stopped after 5 application because of severe erythema.
+ + + Very strong
+ + Strong
+ Moderate
− Absent
DMA Dimethylangelicin
TMA Trimethylangelicin

Toxicity of the 6-alkylangelicins

The 6-alkylangelicins show a small toxicity, lower than that of 8-MOP (8-metoxypsoralen), the drug of first choice for the PUVA therapy. For example the 6,4'-dimethylangelicin, administered in methylcellulose suspension, show an acute toxicity having the following values, expressed in terms of LD$_{50}$ in mice:

| per i.p. (intraperitoneum) | 0.75 g/Kg | (0.3 g/Kg for 8-MOP) |
|---|---|---|
| per os | >2 g/Kg | (0.75 g/Kg for 8-MOP). |

Therapeutical activity of the 6-alkylangelicins

The genotoxicity, in terms of mutagenic activity, of 6-alkylangelicins is much lower than that of 8-MOP (Table V).

TABLE V

Mutagenic activity of 6-alkylangelicins on *E. coli* WP2-uvr A by irradiation with UV-A (a).

| Furocoumarin | no of mutants per 10$^6$ survivors irradiation time (seconds) | | | | |
|---|---|---|---|---|---|
| | 10 | 20 | 30 | 60 | 90 |
| 8-MOP (b) | 0.4 | 1.15 | 1.5 | 3.1 | 7.0 |
| 6,4-dimethylangelicin | 0.24 | 0.7 | 0.99 | 1.83 | — |
| 6,4'-dimethylangelicin | 0.96 | 1.76 | 2.63 | — | — |
| 6,4,4'-trimethylangelicin | 0.84 | 1.18 | 1.24 | 1.98 | — |
| 6,4,5'-trimethylangelicin | 0.62 | 0.91 | 1.23 | 1.93 | — |

(a) The test was performed at the furocoumarin concentration of 5 µg/ml according to Venturini et al., Chem.-Biol. Interactions, 30, 203, 1980.
(b) As reference compound.

The therapeutical effectiveness of two 6-alkylangelicins, that is 6,4'-dimethylangelicin and 6,4,4'-trimethylangelicin, which have been chosen among the various new compounds on the basis of their antiproliferative activity, of their low genotoxicity and of their absence of skin phototoxicity on guinea-pig skin, were tested by measuring their capacity to clear psoriatic lesions in various patients (see Table IV).

For a comparative evaluation, the efficacy of 8-MOP (8-methoxypsoralen), the most used agent for PUVA, has also been tested in the same experimental conditions.

In the treated patients various areas 4×4 cm of the affected skin were used:

a) in the first area an ethanolic solution (0.1% W/V) of the compound under investigation, was applied until a concentration of 5 µg/cm$^2$ was reached and left to evaporate by the heat of the body (or by hot air stream).

After 20 minutes the area was irradiated with a high intensity UV-A emitting low pressure mercury fluorescent lamp type PUVA WALDMANN SYLVANIA F 15 T S.

The irradiation doses were selected in the range between 2.5-13 J/cm$^2$; in particular the initial dose was 2.5 J/cm$^2$ and this was gradually increased till 13 J/cm$^2$ was reached on the basis of the skin tolerance.

b) In a second area an ethanolic solution of 8-methoxypsoralen (8+MOP) was applied to a concentration of 5 µg/cm$^2$ and the area was irradiated in a strictly similar way as in a).

c) a third area was treated in the same way as area a), but was not irradiated with UV-A;

d) a fourth area was irradiated as in a) with the same dose of UV-A light in the absence of any compound.

The treatment with the two 6-methylangelicins was repeated generally 5 times a week for 2 or 3 weeks. A good clearing of the psoriatic lesions was generally observed after 9 treatments, while in the case of 8-MOP for the same treatments the extent of clearing was clearly lower (about 80%). In addition 6-methylangelicins appeared to be entirely uncapable of inducing skin-erythema even in the patients in which 8-MOP induced severe phototoxic response.

The area treated with the angelicin derivatives but not with UV-A did not show any improvement, while the area treated with UV-A alone showed a very low improvement.

While 6,4'-dimethylangelicin induced an evident dark pigmentation in the treated area, less pronounced than that induced by 8-MOP in the same conditions, 6,4,4'-trimethylangelicin appears more active.

The antiproliferative activities have been documented by hystological examinations of bioptical specimens carried out on the tested areas, soon after the treatment and one month later.

The strong activity of the 6-alkylangelicins according to the invention in inhibiting the epidermal DNA synthesis of mice after oral administration (see Table VI) allows to consider these compounds effective also by oral administration in humans and UV-A irradiation.

The following pharmacological compositions may be used for oral administration of the 6-alkylangelicins:

Capsules:

-continued

| | |
|---|---|
| 6-alkylangelicin (drug) | 30 mg |
| Lactose (diluent) | 70 to 120 mg |
| Mg stearate (lubricant) | 1 to 1.5 mg |
| Na Lauril sulphate (wetting) | 1.5 mg |
| contained in a convenient hard or soft gelatine capsule. | |
| Tablets | |
| 6-alkylangelicin (drug) | 30 mg |
| Lactose (diluent) | 240 mg |
| Mg stearate (lubricant) | 2 mg |
| Maize starch (disintegrant and lubricant) | 60 mg |
| Microcrystalline cellulose (lubricant and disintegrant) | 10 mg |
| Polyvinylpyrrolidone (binder) | 3% |
| Na Lauril sulphate (wetting) | 3 mg |
| one or more capsules or tablets, according to the body weight, age and sex of the patient, to be orally administered two hours before irradiation. | |

TABLE VI

Inhibition of epidermal DNA synthesis in the mouse "in vivo" after oral administration of the compound (250 mg/kg) and UV-A irradiation (9 J/cm$^2$) (a).

| FUROCOUMARIN | % inhibition ± S.E. |
|---|---|
| angelicin (b) | 28.0 ± 2 |
| 8-MOP (b) | 39.1 ± 3.7 |
| 6-methylangelicin | 19.65 ± 9.2 |
| 6,4-dimethylangelicin | 58.4 ± 13.0 |
| 6,4,5'-trimethylangelicin | 36.8 ± 8.5 |
| 6,4,4'-trimethylangelicin | 67.72 ± 8.2 |
| 6,5,5'-trimethylangelicin | 60.6 ± 14.1 |
| 6,5-dimethylangelicin | 50.12 ± 19 |
| 6,4'-dimethylangelicin | 49.23 ± 8.0 |
| 6,5'-dimethylangelicin | 22.48 ± 12.0 |

(a) Determined according to Bordin et al., Il Farmaco, Ed.Sc., 36, 506, 1981.
(b) Reference compounds.

We claim:

1. Process of producing alkylangelicins free from psoralens, of formula (1)

wherein R is alkyl, $R_1,R_2,R_3,R_5$ are independently hydrogen or alkyl, $R_6$ is hydrogen, alkyl, hydroxymethyl, acetoxymethyl, metoxymethyl, as well as aminomethyl, alkylaminomethyl, dialkylaminomethyl or a group of formula wherein $R_7$ and $R_8$ are simultaneously hydrogen, methyl or ethyl, free or salified, characterized in that a 6-alkylumbelliferone O-derivative of formula

(2)

wherein $R,R_1,R_3$ have the meaning above referred to, and $R_4$ is an acyl residue of formula

—CO—$R_9$ wherein $R_9$ is an alkyl or an allyl residue of formula

—CHR$_{10}$—CH=CHR$_{11}$ wherein $R_{10}$ and $R_{11}$ are independently hydrogen or alkyl, or a β-ketoalkyl residue of formula

—CHR$_{12}$—CO—CH$_2$R$_{13}$ wherein $R_{12}$ and $R_{13}$ are independently hydrogen or alkyl, is submitted to direct alkaline cyclization or to appropriate Fries or Claisen rearrangements and successive cyclization, thus yielding compound (1), wherein $R_5$ and $R_6$ are independently hydrogen or alkyl groups, and, when $R_6$ of compound (1) is hydrogen, it is converted, through a treatment with chloromethylmethylether into the corresponding 4'-chloromethylangelicin, which is then converted into the corresponding 4'-hydroxymethyl, 4'-acetoxymethyl, 4'-aminomethyl, 4'-alkylaminomethyl, 4'-dialkylaminomethyl or 4'-aminoethoxymethyl or dimethylaminoethoxymethyl or 4'-diethylaminoethoxymethyl or 4'-diethylaminoethoxymethyl derivatives and finally, to obtain water-soluble compounds, the derivatives containing the amino group, substituted or not, are converted into the corresponding hydrochlorides.

* * * * *